United States Patent [19]
Chang et al.

[11] Patent Number: 5,192,403
[45] Date of Patent: Mar. 9, 1993

[54] CYCLIC VOLTAMMETRIC METHOD FOR THE MEASUREMENT OF CONCENTRATIONS OF SUBCOMPONENTS OF PLATING SOLUTION ADDITIVE MIXTURES

[75] Inventors: I-Chia H. Chang, Peekskill; Wilma J. Horkans, Ossining, both of N.Y.

[73] Assignee: International Business Machines Corporation, Armonk, N.Y.

[21] Appl. No.: 701,278

[22] Filed: May 16, 1991

[51] Int. Cl.[5] ............................................. G01N 27/26
[52] U.S. Cl. ................................ 204/153.1; 204/402; 204/434
[58] Field of Search ...................... 204/153.1, 402, 434

[56] References Cited

U.S. PATENT DOCUMENTS

| | | | |
|---|---|---|---|
| 4,146,437 | 3/1979 | O'Keefe | 204/434 |
| 4,668,346 | 5/1987 | Entwistle | 204/402 |
| 4,725,339 | 2/1988 | Bindra et al. | 204/434 |
| 4,786,373 | 11/1988 | Salcheimo et al. | 204/402 |
| 4,917,774 | 4/1990 | Fisher | 204/402 |
| 4,917,777 | 4/1990 | Fisher | 204/402 |

OTHER PUBLICATIONS

"Cyclic Voltammetric Stripping Analysis of Acid Copper Sulfate Plating Baths", by Haak, Ogden and Trench, Plating and Surface Finishing, Apr. 1981.
"Cyclic Voltammetric Stripping Analysis of Acid Copper Sulfate Plating Baths", Haak, Ogden and Trench, Plating and Surface Finishing, Mar. 1982.
"Introducing The Biggest Advance in Plating Bath Analysis Since The Hull Cell", UPA Technology, Inc. Copyright 1983.
"Take the guesswork out of plating bath control", ECI Technology, ECI Technology, Copyright 1989.

Primary Examiner—John Niebling
Assistant Examiner—Bruce F. Bell
Attorney, Agent, or Firm—Sterne, Kessler, Goldstein & Fox

[57] ABSTRACT

A cyclic voltammetric method for measuring concentrations of subcomponents of additive mixtures, comprising the steps of: (a) preparing a basis solution which contains all of the components of an unknown solution to be measured, except a component of interest; (b) preparing a calibration solution which contains the component of interest in a known concentration near that which would be expected in the unknown solution; (c) adding measured amounts of the calibration solution to a first defined volume of the basis solution and plotting a first cathodic charge against the added volume of the calibration standard; (d) adding measured amounts of the unknown solution to a second volume of the basis solution and plotting a second cathodic charge against the added volume of the unknown solution; and (e) comparing the slopes of the first and second curves to determine the concentration of the component of interest in the unknown solution.

7 Claims, 6 Drawing Sheets

CYCLIC VOLTAMMETRIC METHOD FOR THE MEASUREMENT OF CONCENTRATIONS OF SUBCOMPONENTS OF PLATING SOLUTION ADDITIVE MIXTURES

TECHNICAL FIELD

The present invention relates to a cyclic voltammetric method for measuring concentrations of subcomponents in additive mixtures. More particularly, the invention relates to an improved cyclic voltammetric method for measuring the concentration of an unknown subcomponent in the additive mixture. Still more particularly, the invention relates to a method for measuring and ultimately controlling the concentrations of subcomponents of additive mixtures in a plating solution.

BACKGROUND ART

Acid-Cu plating is an old and successful technology. Although simple in principle, it relies in general practice on the use of proper additives to determine the properties of the Cu deposit. All additive systems consist of at least two chemicals, and usually more, at low concentrations in the plating solution. If the concentrations change, or if the additive components get out of balance, the quality of the plated Cu deteriorates. Monitoring and control of additives is thus very important, especially as the technological demands on the Cu become more stringent. However, no really good additive control techniques are known to exist in the art. Additive control in Cu plating is a major scientific and technological challenge.

One method proposed for additive monitoring is cyclic voltammetry ("CV"). The CV technique has been described by R. Haak, C. Ogden, and D. Tench, *Plating* 64(4):52 (April 1981) and 65(3):62 (March 1982). The basis of CV analysis is that the additives change the polarization of the Cu-deposition reaction and therefore affect the amount of Cu deposited in a linear potential sweep applied to an inert electrode in the plating solution. The measured copper plating charge is used as a measure of the additive concentration.

Cyclic voltammetry analyses are most commonly called cyclic voltammetry stripping ("CVS") and use the stripping or anodic charge as a measure of the amount of plated copper. The use of the stripping charge gives inferior results for analyses of Cu additives. Acid Cu plates with essentially 100% current efficiency as a two-electron reduction of $Cu^{2+}$. In the presence of additives, however, Cu strips in a combination of +1 and +2 oxidation states. The stripping charge can therefore give an erroneous measure if it is assumed to be the same as the plating charge. The direct measurement of the plating charge presents no problem, however, with the proper instrumentation.

Despite claims that CV can be used as a monitoring tool (and the availability of a commercial CVS instrument), many serious questions about the technique still arise. The method does not measure a quantity that can be directly related to the concentration of components of a known solution. Additionally, one quantity, a charge, is used to estimate the solution level of a multi-component additive. For CV monitoring to be useful, the ratios of the components of the additive system must remain constant as the additive is consumed.

The present invention overcomes the deficiencies and problems associated with the conventional technology.

DISCLOSURE OF THE INVENTION

The present invention comprises the steps of (a) preparing a Basis Solution which contains all of the components of the plating solution to be measured (the "unknown solution"), except the component of interest; (b) preparing a calibration solution which contains the component of interest in a known concentration near that which would be expected in the unknown; (c) adding measured amounts of the calibration solution to a first defined volume of the Basis Solution, performing cyclic voltammetry, and plotting the cathodic copper plating charge against the added volume of the calibration standard; (d) adding measured amounts of the unknown plating solution to a second volume of the Basis Solution, performing cyclic voltammetry, and plotting the cathodic copper plating charge against the added volume of the unknown mixture; and (e) comparing the slopes of the calibration standard curve and the unknown mixture curve to determine the concentration of the component of interest in the unknown solution.

BRIEF DESCRIPTION OF DRAWINGS

The foregoing and other features and advantages of the invention will be apparent from the following more particular description of preferred embodiments of the invention, as illustrated in the accompanying drawings.

BEST MODE FOR CARRYING OUT THE INVENTION

Figure 1:
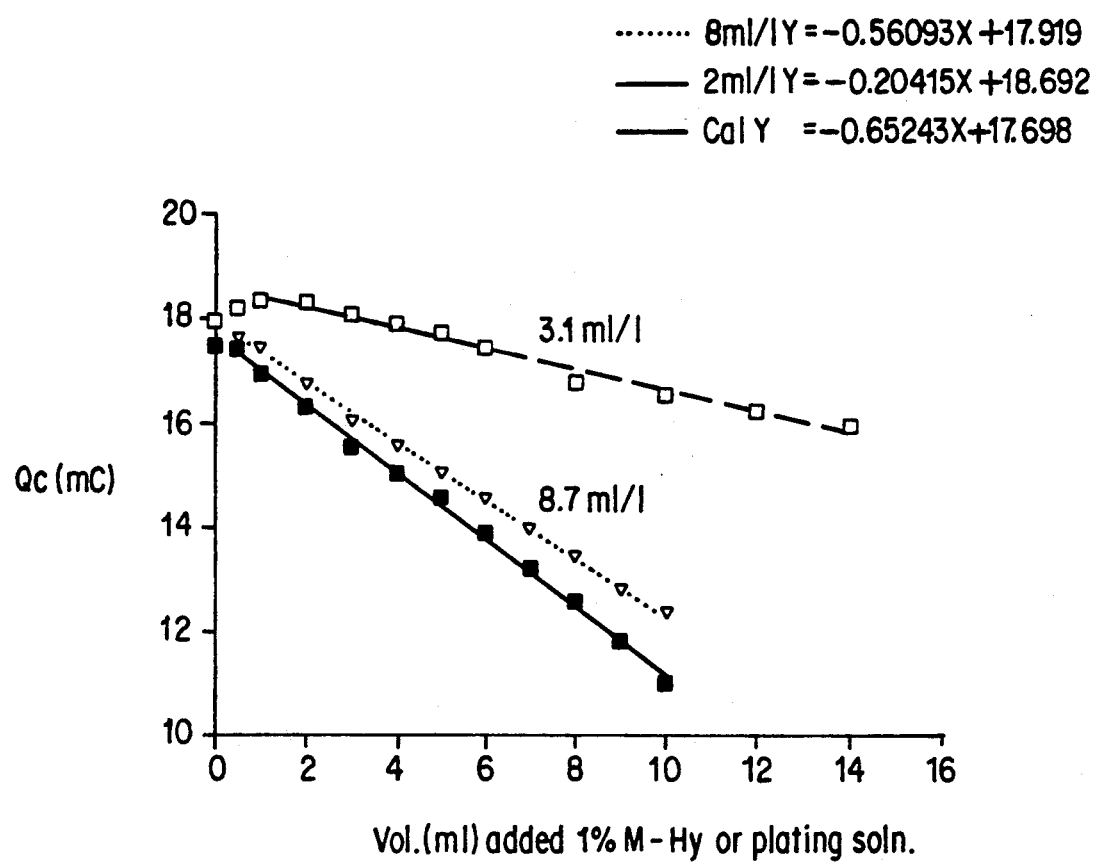
FIG. 1 shows the results of a standard cyclic voltammetric analysis of an acid-Cu plating solution containing a known concentration of M-Hy (the additive of SelRex Cubath ® acid-Cu plating solution) at three different concentrations.

This invention relates to a modification of the CV technique that makes it selective for only one part of a multi-component plating additive system. The other component(s) can be monitored by a different analytical technique, such as ion chromatography.

Reduced to its essentials, the method of this invention comprises the following steps:

(a) prepare a Basis Solution which contains all of the components of the solution to be measured (the "unknown solution"), except the component of interest;

(b) prepare a calibration solution which contains the component of interest in a known concentration near that which would be expected in the unknown;

(c) add measured amounts of the calibration solution to a first defined volume of the Basis Solution and plot the copper plating (cathodic) charge in cyclic voltammetry in the mixed solution (the "calibration standard") versus the volume of standard added;

(d) add measured amounts of the unknown solution to a second volume of the Basis Solution and plot the copper plating (cathodic) charge in cyclic voltammetry in the mixed solution versus the volume of unknown added; and (e) compare the slopes of the calibration standard curve and the unknown mixture curve to determine the concentration of the component of interest in the unknown solution.

The method of the invention can be applied to many types of situations where it is desired to determine an unknown component in a multi-component solution. It is particularly useful in monitoring plating solutions, where it is desired to control the composition of the solution for consistency of the deposit properties. Once the concentration of the component of interest has been determined, it is a relatively simple matter to apply this value to a control system (either manual or automated) to adjust the concentration of the component of interest in the working solution.

The technique of this invention can be used to monitor and control many types of plating solution additives. A preferred embodiment of the invention will be illustrated as a monitor for the Cubath® M-Hy 70/30, an additive for acid-Cu plating sold by SelRex, a division of OMI International Corp., 21441 Hoover Road, Warren, Mich. 49089. This additive can be purchased as a single addition agent or as two components: MD and M-Lo (MD and M-Lo are trade names for proprietary products of SelRex). The MD, which is not a solution of a pure chemical, is called by SelRex the Carrier and functions as a brightener. It can be determined quantitatively by high performance liquid chromatography ("HPLC"). None of the other Cubath® M-Hy ingredients has an HPLC peak. The M-Lo is itself a combination of two components, called by SelRex a Leveller and a Ductilizer, but these are very rarely replenished separately.

In order to understand the modification in the CV procedure which comprises this invention, it is necessary first to describe a more standard approach. For CV analysis of the entire Cubath® M-Hy 70/30 additive, the procedure described below can be used, employing the following materials: (1) a stock solution consisting of $CuSO_4$, $H_2SO_4$, and $Cl^-$ at approximately the same concentrations as in the plating solution; (2) a standard solution containing a known concentration of the additive in $H_2O$ (for example, 10 ml/l M-Hy); and (3) the unknown plating solution. A calibration run and an analysis are done sequentially as follows:

A. Calibration

1. Measure a known volume of the stock solution into an electochemical cell (described in more detail below).
2. Cycle the potential of the working electrode and determine the Cu-plating charge.
3. Add a small aliquot of the M-Hy standard to the stock solution in the cell
4. Cycle the potential again and measure the Cu-plating charge.
5. Repeat steps A.3 and A.4. Plot the charge versus the added volume to obtain a calibration curve.

B. Analysis

1. Measure a known volume of the stock solution into the electrochemical cell.
2. Cycle the potential applied to the working electrode and determine the Cu-plating charge.
3. Add a small aliquot of the unknown plating solution to the stock solution in the cell.
4. Cycle the potential again and measure the Cu-plating charge.
5. Repeat steps B.3 and B.4. Plot the charge versus the added solution volume to obtain a similar curve for the unknown.

The dependence dQ/dV, where Q is the copper plating charge and V is the added volume of standard or unknown, is not linear. However, a good approximation to linearity will be found as long as the added volume is small compared to the total solution volume in the cell. Under these conditions, the concentration of the unknown can be determined from the slopes of the calibration and analysis curves and from the known concentration of the standard solution.

FIG. shows the application of the above-described procedure to plating solutions of known M-Hy concentration. Good results are obtained. Solutions that were prepared to be 2 and 8 ml/l in M-Hy were found by the CV analysis to be 3.1 and 8.7 ml/l, respectively.

If the MD/M-Lo ratio changes, however, the standard procedure is no longer applicable. This was shown by the following example.

Figure 2:
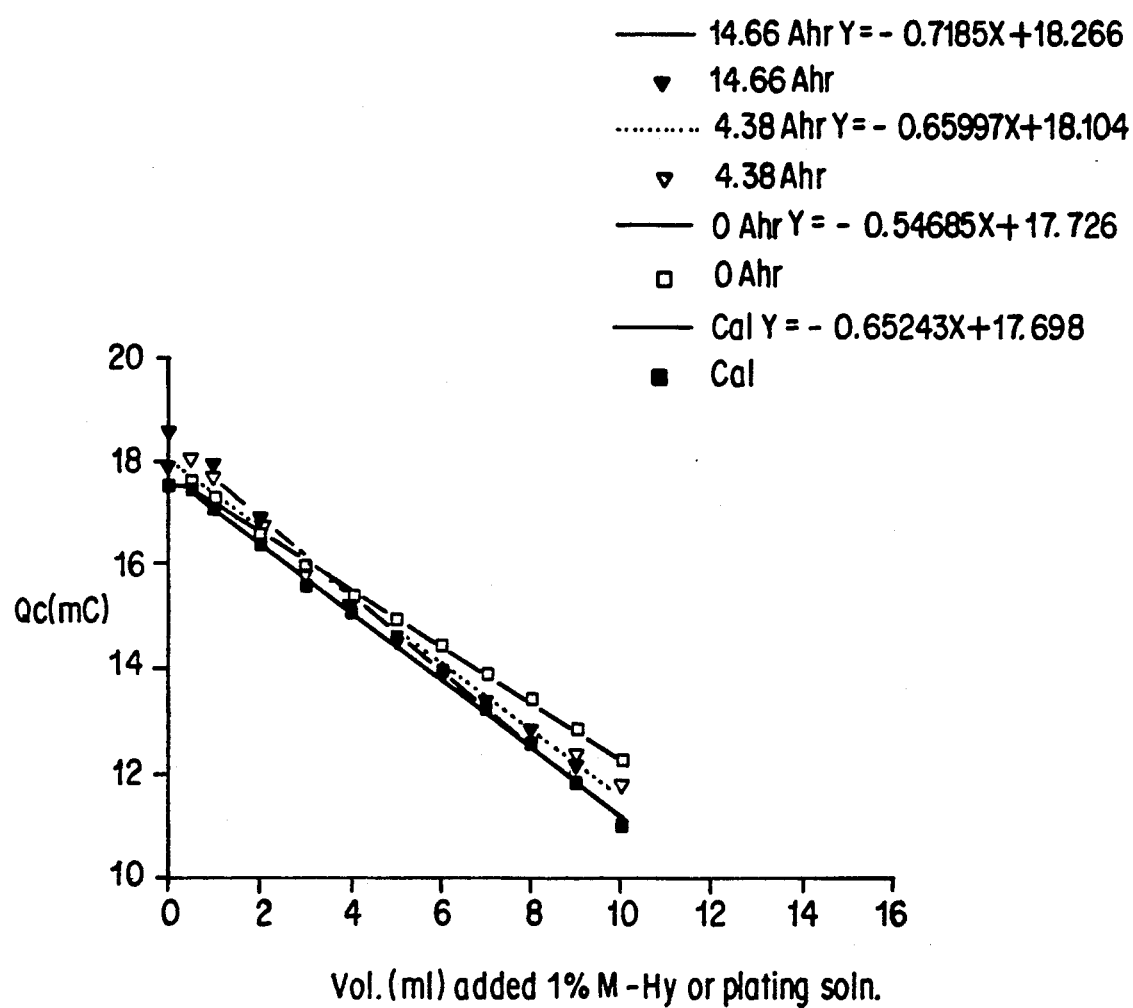
FIG. 2 shows the results of a standard cyclic voltammetric analysis of a working plating solution, sampled after the passage of various amounts of charge.

A working plating solution was investigated. The total charge passed was low, and the expected depletion rate would predict a negligible change in the additive concentration. The solution, however, was found by HPLC to be depleted in MD. This working solution was still plating high-quality Cu and probably still contained nearly the original amount of M-Lo. The standard CV procedure (described above) gave the results of FIG. 2 for this working solution sampled after the passage of various amounts of Cu plating charge. The increase in slope dQ/dV with charge passed in the solution does not imply an increase in additive concentration (a physical impossibility). Rather, it shows that the calibration slope is not correct for the MD/M-Lo ratio in the unknown (the working solution).

Figure 3:
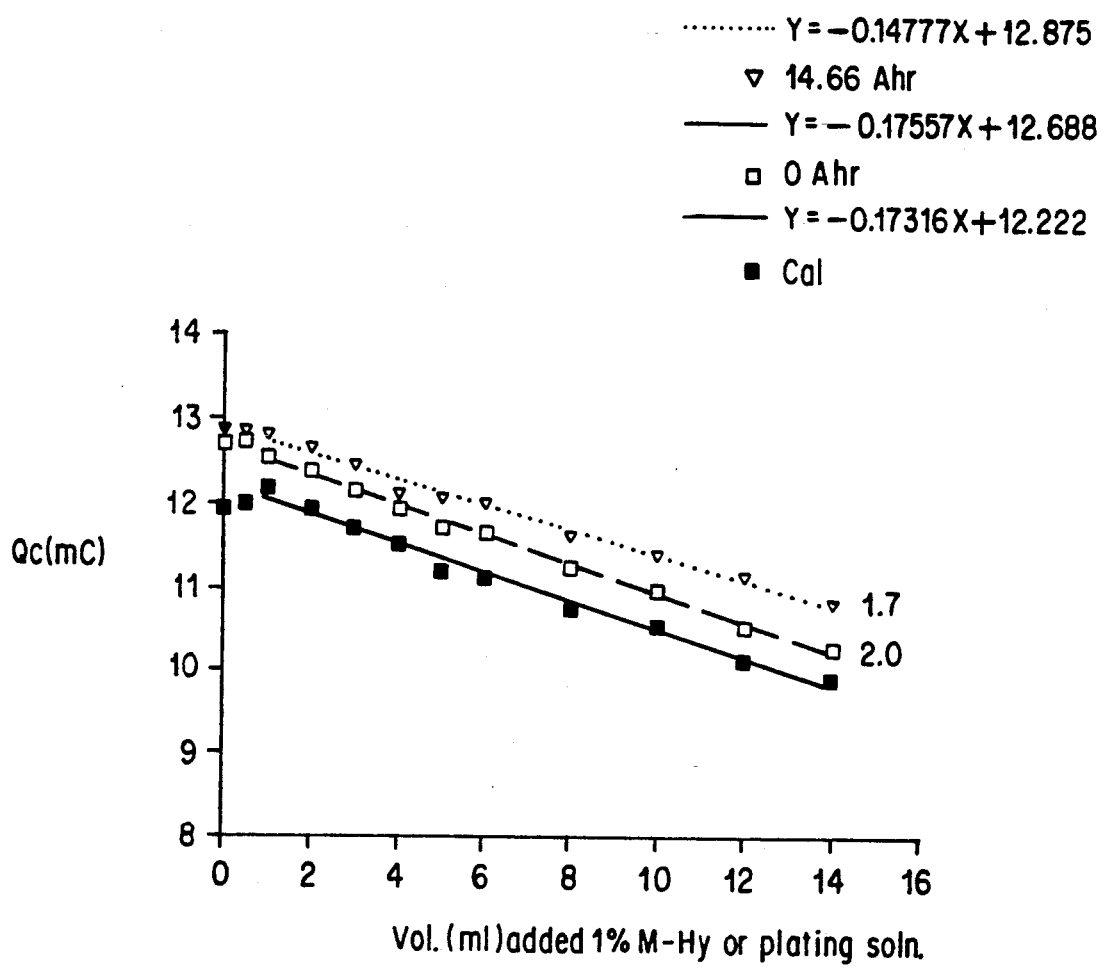
FIG. 3 shows the results of an analysis on the same plating solutions as in FIG. 2, using the techniques of this invention to determine the M-Lo component of the M-Hy additive system.

The MD level can be determined by HPLC. The present invention takes advantage of this to use the CV to monitor the M-Lo level alone. This, however, requires that the CV analysis be made insensitive to MD. In order to determine the M-Lo level independent of MD concentration, the standard procedure is modified by adding MD to the stock solution in the cell. For the examples that follow, 5 ml/l of MD was added to the stock solution of step 1 in both the calibration and the analysis. A reanalysis of the working plating solutions of FIG. 2, using the modified procedure of this invention, is shown in FIG. 3. The 0 Ahr sample, which is slightly low in MD (as determined by HPLC) and the 14.66 Ahr sample (found to contain no detectable MD) are both found, by the CV procedure of this invention, to have about the expected M-Lo concentrations.

Figure 4:
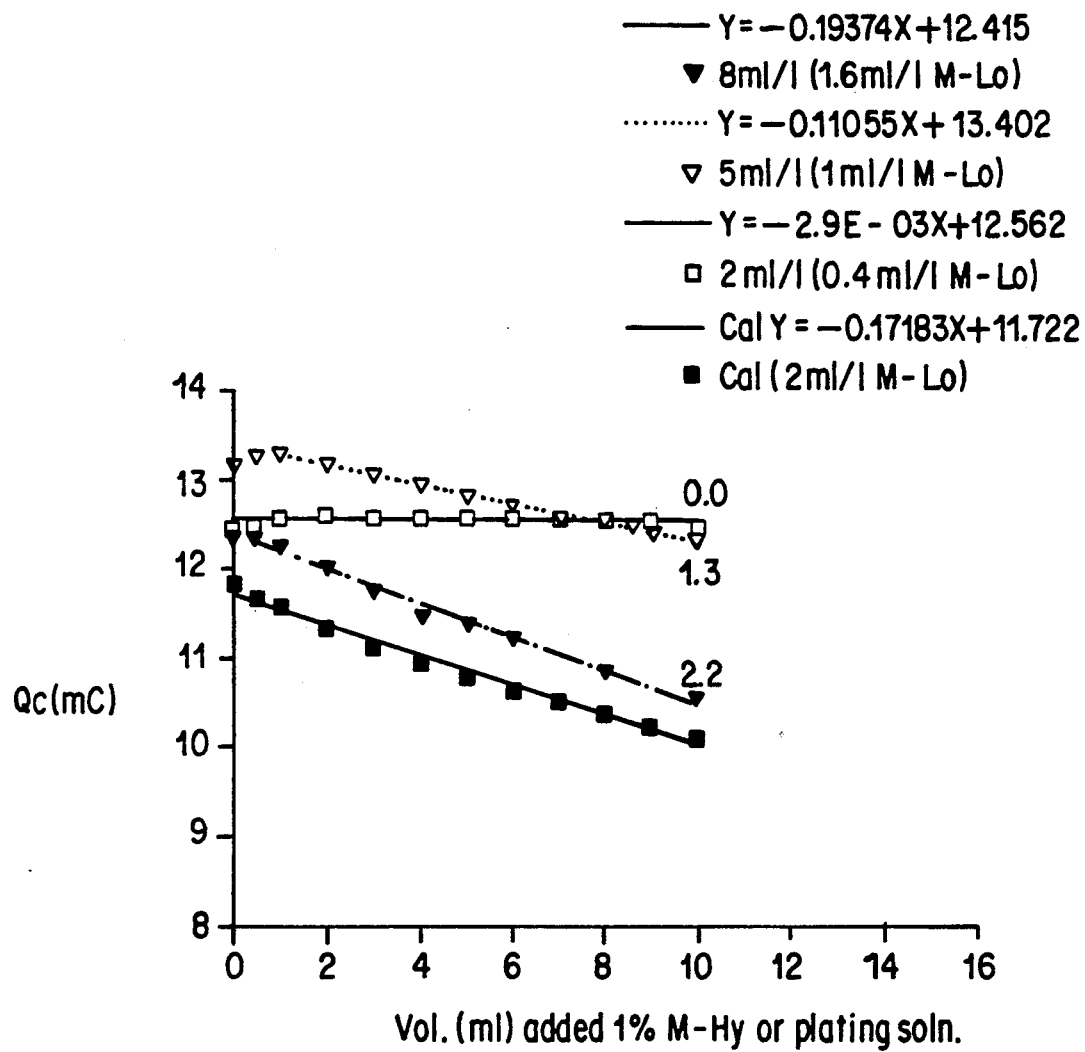
FIG. 4 shows the results of analyses of M-Lo in a first example using the techniques of this invention on plating solutions over a range of M-Hy concentrations.

The modified CV technique of this invention has been shown to work over a range of Cubath® M-Hy concentrations; the results are shown in FIG. 4. At 2 ml/l M-Hy (which is 0.4 ml/l M-Lo), the M-Lo is below the detection limit in this example. (Improved sensitivity has been obtained by refinements of the technique as described in Example 2 below.) A 5 ml/l M-Hy solution (1 ml/l in M-Lo) and an 8 ml/l M-Hy solution (1.6 ml/l in M-Lo) were found by the analysis to be 1.3 and 2.2 ml/l in M-Lo, respectively.

Figure 5:
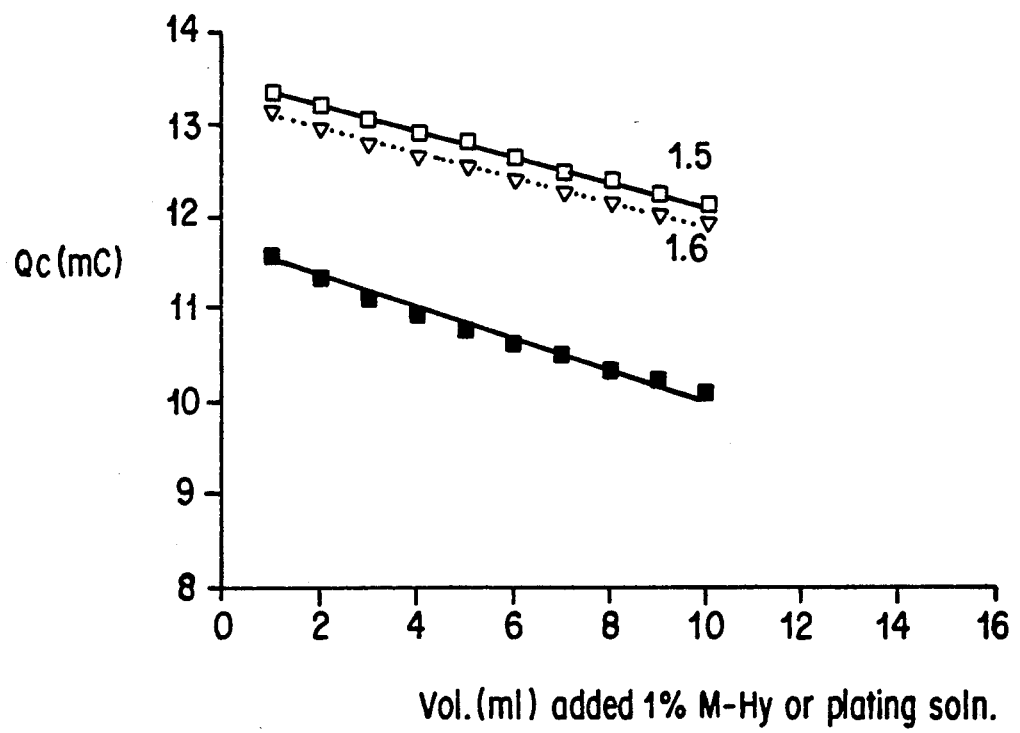
FIG. 5 shows the results of analyses of M-Lo using the techniques of this invention on plating solutions in which the MD of the depleted working solution was replenished.

The MD of the depleted working solution was replenished to its original level of 6.4 ml/l without adding M-Lo. Both the depleted solution (14.7 Ahr) and the replenished solution (26.1 Ahr) were analyzed; the results are shown in FIG. 5. Both showed M-Lo levels very near the expected level of 1.6 ml/l.

Cu plating solutions with a fixed level of 1.6 ml/l of M-Lo and MD levels in the range of 0-8 ml/l were investigated. The slope of the CV M-Lo determination was found to be independent of the MD levels in these artificial unknowns. Thus the method has been shown to determine the M-Lo level independent of the MD level.

The technique of this invention has been shown greatly to improve and to quantify the standard CV monitoring technique for acid-Cu additives. Preliminary tests indicate that this technique will also work for other additive solutions having a different chemical composition.

The improved cyclic voltammetric (CV) determination of one component of a multi-component additive for acid-Cu plating will be illustrated in two examples for the additive SelRex Cubath ® M-Hy 70/30. The M-Hy has two major components, the Carrier MD and the Leveller/Ductilizer M-Lo. The M-Lo is treated as a single component for the purposes of this illustration.

EXAMPLE 1

In this example, the working plating solution, the unknown in the M-Lo analysis, had the following composition:

| | | |
|---|---|---|
| $CuSO_4.5H_2O$ | 67 g/l | 0.27M |
| $H_2SO_4$ | 92.5 ml/l | 1.7M |
| $Cl^-$ | 70 mg/l | |
| MD | unknown | |
| M-Lo | unknown | |

The cyclic voltammetry was carried out in a "Basis Solution" having approximately the same composition as the unknown to be analyzed. The Basis Solution contained all of the components except the additive component to be analyzed. In this example, the Basis Solution contained all components except M-Lo.

The MD component of the additive should be included in the Basis Solution near the concentration at which it will be maintained in the working Cu-plating solution. Plating solutions have a make-up MD concentration of 6.4 ml/l but typically have a lower working concentration. The principle is that additions of the unknown to the Basis Solution will not change the MD concentration in the test cell sufficiently to affect the analysis.

The Basis Solution used in the analysis is shown below. Variations on the MD level could be found that could also result in valid analyses.

| | | |
|---|---|---|
| $CuSO_4.5H_2O$ | 67 g/l | 0.27M |
| $H_2SO_4$ | 92.5 ml/l | 1.7M |
| $Cl^-$ | 70 mg/l | |
| MD | 5 ml/l | |

A given volume of Basis Solution was pipetted into a standard electrochemical cell. The cell contained a working electrode, a counter electrode (electron source or sink), and a reference electrode. The working electrode was made of an inert metal. In this example, a commercial Pt rotating disk electrode ("RDE") (having a Teflon sheath), with an area of 0.200 cm$^2$, was used as the working electrode. The area of the electrode is not critical. The RDE was rotated at a fixed rate in order to give well-defined conditions of mass transport during the analysis. Platinum is the preferred material of the working electrode, although other inert electrodes could conceivably be used.

The counter electrode was a Pt foil with an area that was large compared to the area of the working electrode. The reference electrode was a mercurous sulfate electrode ("MSE") (Hg/Hg$_2$SO$_4$, sat. K$_2$SO$_4$), which has a potential of 0.64 V on the hydrogen scale. Other counter electrode materials can be used as long as they are compatible with the system. Other reference electrodes can be used with a proper adjustment of the reference scale.

The potential of the working electrode vs. the reference electrode was controlled by a potentiostat provided with a signal generator. A linear potential sweep of fixed rate between fixed potential limits $E_a$ (the positive limit) and $E_c$ (the negative limit) was applied to the working electrode in order to plate Cu on the electrode in the negative-going part of the cycle and dissolve or strip the Cu during the positive-going part of the cycle.

In this example, a volume of 200 ml of Basis Solution was placed in the cell, but the volume chosen is not critical. In order that the concentrations remained well-defined after volume additions to this original solution, all three electrodes were inserted directly into the cell with no glass frits or other impedances to the free mixing of solution.

The RDE was cleaned by immersion in HNO$_3$ before each analysis. After cleaning, the Pt RDE was introduced into the cell containing the 200 ml of Basis Solution. The RDE was rotated at 1600 rpm. A potential program was set up that cycled the electrode potential at 100 mV/sec between +1.2 V and −0.6 V vs. the reference MSE. The charge was measured with a commercial coulometer that is bi-polar; only the cathodic (reduction) charge was measured. The plating charge was taken as the total cathodic charge during one potential cycle. The potential was cycled until a stable charge reading was obtained, no more than five times.

The next procedure was a calibration step. A calibration standard solution was prepared. The calibration standard solution had known amounts of M-Lo and MD. The level of M-Lo should be chosen to be approximately that expected in the unknown (working solution). In practice, the entire M-Hy 70/30 additive, consisting of 80% MD and 20% M-Lo, was used at a concentration of 10 ml/l in the standard solutions. Other levels of M-Hy may be appropriate, depending on the solutions being analyzed. The calibrating solution used in the example had the composition:

| | | |
|---|---|---|
| $CuSO_4.5H_2O$ | 67 g/l | 0.27M |
| $H_2SO_4$ | 92.5 ml/l | 1.7M |
| $Cl^-$ | 70 mg/l | |
| MD | 8 ml/l | |
| M-Lo | 2 ml/l | |

Incorporation of the first three components is not essential, but gives a better result.

A 0.5 ml aliquot of the calibration standard solution was pipetted into the cell containing the Basis Solution. The RDE served to mix the solution in the cell. Potential cycling was continued as the addition was made. The cathodic charge was read after the charge reading had stabilized (not more than five potential cycles should be needed; if more are required, there may be a problem with the solution, the equipment, the analysis, etc.). A second 0.5 ml aliquot of the standard solution was added to the cell and the procedure repeated. Then the procedure was repeated with 1.0 ml additions to a total of at least 10 ml to ensure a significant change in the measured charge while remaining within the linear region of the charge-volume curve.

The value of cathodic charge Q was plotted versus the volume V of standard solution added to the Basis Solution. Omitting the first (zero-addition) point, the data were fitted with a least-squares linear fit to obtain the slope dQ/dV for the standard solution. This is shown by the solid line in FIG. 4.

The next procedure was an unknown determination step. The electrochemical cell was cleaned; the Pt RDE was cleaned again as described above. A second volume of the same Basis Solution was pipetted into the cleaned cell and the RDE replaced. The procedure for the unknown was exactly the same as that for the calibration step, except that the solution added to the Basis Solution was the plating solution with an unknown M-Lo level. The slope dQ/dV was determined for the unknown. Examples for three M-Lo concentrations are shown in FIG. 4.

The concentration of M-Lo in the unknown, when the standard has an M-Lo concentration of $C_{std}$, is given by the following expression:

$$((dQ/dV)_{unk}/(dQ/dV)_{std}) \times C_{std}$$

This relationship holds as long as the conditions of the calibration and analysis are identical.

EXAMPLE 2

Figure 6:
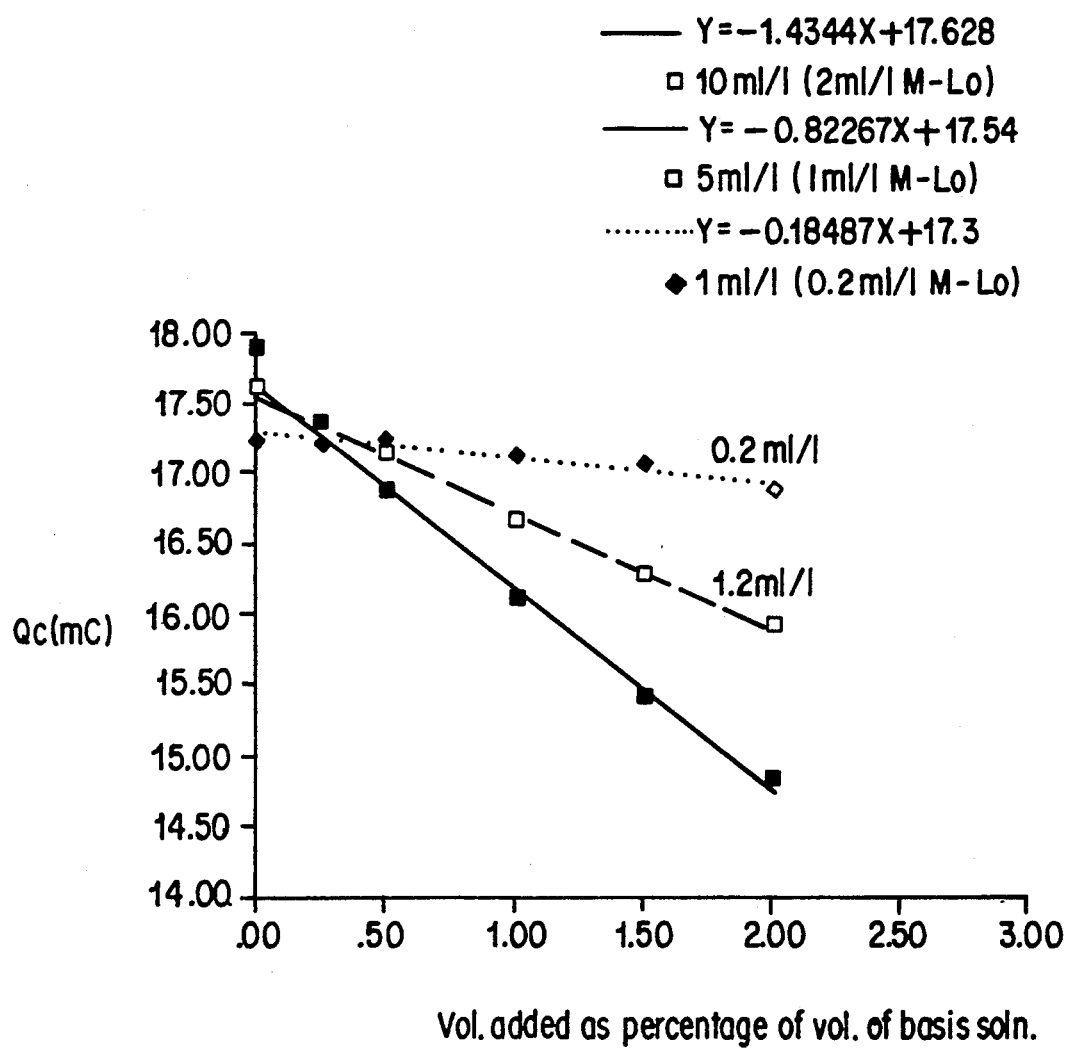
FIG. 6 shows the results of analyses of M-Lo in a second example using the techniques of this invention on plating solutions over a range of M-Hy concentrations.

This example is essentially the same as Example 1, with the following differences:

a. A Pt RDE with an area of 0.458 cm$^2$ was used. The measured charge scales directly with the electrode area. As long as the same electrode is employed in the calibration and in the measurement of the unknown, the electrode area does not affect the procedure.

b. The volume of basis solution first added to the cell was 100 ml. This change is unimportant as long as the original volume and the volume of the additions are known.

c. A more stringent cleaning procedure was used to clean the Pt RDE. In this example, the cleaning step was performed in a separate cell (also having a Pt counter electrode and a mercurous sulfate reference electrode). The cell contained 0.1M $H_2SO_4$ of a high level of cleanliness. The RDE was cleaned by a potential cycling. The potential of the working electrode was controlled by a potentiostat with a signal generator supplying the potential program. While rotating the RDE at 400 rpm, the potential was swept for 10 min at a sweep rate of 400 mV/sec between the potential limits of +1.4 V and −0.7 vs. the reference MSE. Other potential programs and conditions can also result in electrode cleaning.

d. Fewer data points were taken than in Example 1 (see FIG. 6), and the total added volume was a smaller percentage of the volume of solution in the cell. The addition procedure in Example 2 was the same as in Example 1, except that the first two aliquots were each 0.25 ml, and the remaining aliquots added were 0.5 ml each to a total addition of 2 ml in the 100 ml volume. The use of fewer points speeds up the determination. The use of a smaller total added volume better keeps the measurement in the region of linearity and gives much better results. In Example 1, the 2 ml/l M-Hy (0.4 ml/l M-Lo) was below the limits of detection. With the improved procedure, however, even 1 ml/l M-Hy (0.2 ml/l M-Lo) was within the detection limits.

The present invention has the following features that are not found in heretofore known measurement techniques:

1. The invention does more than simply directly measure the cyclic voltammetry behavior in unknown and standard solutions. Rather, small additions of either an unknown or a known solution are added to a large volume of "basis" solution and the Cu-plating charge in cyclic voltammetry is measured as a function of the addition volume. The ratio of slopes of the two curves gives the concentration of the additive of interest in the unknown.

a. The use of the same basis solution for the calibrating and unknown solutions makes the procedure insensitive to differences between the two.

b. The major solution components (for example, CuSO, $H_2SO_4$, Cl$^{31}$ ion) are present in both the basis solution and the known or unknown solution, and change negligibly in concentration during the experiment.

2. Cyclic voltammetry can be used for a quantitative monitoring of only one component of a multiple-component system. The analysis technique of this invention is purposely made insensitive to the other solution components. This is achieved by including in the basis solution the component that one does not wish to determine. This other component is monitorable by a separate method, such as ion chromatography.

3. The method is not CVS (cyclic voltammetry stripping), but rather CV directly measuring the plating charge.

a. Although measuring the stripping charge is preferred for metals that do not plate at 100% current efficiency, the stripping charge is not a good measurement for Cu, because Cu can strip in both the +1 and +2 oxidation states in the presence of typical additives in acid sulfate solutions (L. S. Melnicki, in *Proc. Symp. on Electrochemical Technology in Electronics* 88-23, L. T. Romankiw and T. Osaka (eds.) (The Electrochemical Society, Pennington, N.J., 1988), p. 95).

b. Since the number of coulombs/equivalent is thus ill-defined during stripping, the stripping charge is a poor measurement of the amount of Cu that was deposited during the plating portion of the cycle.

c. Use of the plating charge is acceptable, since Cu plates from acid sulfate solutions with essentially 100% current efficiency.

While the invention has been particularly shown and described with reference to preferred embodiments thereof, it will be understood by those skilled in the art that various changes in form and details may be made therein without departing from the spirit and scope of the invention.

We claim:

1. A cyclic voltammetric method for measuring concentrations of subcomponents of additive mixtures, comprising the steps of:
   (a) preparing a basis solution which contains all of the components of an unknown solution to be measured, except a component of interest;
   (b) preparing a calibration solution which contains said component of interest in a known concentration near that which would be expected in said unknown solution;
   (c) adding measured amounts of said calibration solution to a first defined volume of said basis solution;
   (d) applying an electrical potential to an electrode in the mixed calibration/basis solution and plotting the calibration cathodic charge against the added volume of the calibration solution;
   (e) adding measured amounts of said unknown solution to a second volume of said basis solution;
   (f) applying an electrical potential to an electrode in the mixed unknown/basis solution and plotting the cathodic charge against the added volume of the unknown solution; and
   (g) comparing the slopes of the calibration and unknown cathodic charge versus volume curves to determine the concentration of said component of interest in said unknown solution.

2. A method according to claim 1, comprising the further steps of:
   (h) applying said electrical potential in each of steps (d) and (f) cyclically between predetermined positive ($E_a$) and negative ($E_c$) potentials at a predetermined cycling rate; and
   (i) measuring the respective charge readings of said mixed calibration/basis solution and said mixed unknown/basis solution following each full cycle of applied electrical potential.

3. A method according to claim 2, comprising the further steps of:
   (j) applying said electrical potential in step (d) a predetermined number of times or until a stable charge reading is obtained; and
   (k) measuring the charge reading of said calibration/basis solution with each application of said electrical potential.

4. A method according to claim 3, comprising the further steps of:
   (l) applying said electrical potential in step (f) a predetermined number of times or until a stable charge reading is obtained; and
   (m) measuring the charge reading of said unknown/basis solution with each application of said electrical potential.

5. A cyclic voltammetric method for determining additive components in a mixture of additives in a plating solution, comprising the steps of:
   (a) preparing a basis solution containing all components of the plating solution except the one component to be analyzed in an electrochemical cell containing an electrode to which an electrical potential may be applied;
   (b) adding a predetermined amount of a standard solution containing a known amount of the one component to be analyzed to said basis solution;
   (c) thereafter applying an electrical potential to an electrode in said electrochemical cell following step (b) a predetermined number of times or until a stable charge reading is obtained;
   (d) repeating steps (b)–(c) a predetermined number of times;
   (e) plotting the value of the charge read in step (c) versus the volume of said standard solution added to said basis solution as a result of the repetition of step (b) to obtain a graphical plot having the slope dQ/dV for said standard solution;
   (f) adding to said basis solution a predetermined amount of said working solution containing an unknown amount of the one component to be analyzed;
   (g) thereafter applying an electrical potential to said electrochemical cell following step (f) a predetermined number of times or until a stable charge reading is obtained;
   (h) repeating steps (f)–(g) a predetermined number of times; and
   (i) plotting the value of the charge read in step (g) versus the volume of said working solution added to said basis solution as a result of the repetition of step (f) to obtain a graphical plot having the slope dQ/dV for said working solution;
   (j) comparing the slopes of said standard and working solutions determined from steps (e) and (i) to determine the concentration of said one component in said working solution.

6. A method according to claim 5, comprising the further steps of:
   (k) applying said electrical potential in each of steps (c) and (g) cycling between predetermined positive ($E_a$) and negative ($E_c$) potentials at a predetermined cycling rate; and
   (l) measuring the respective charge readings of said mixed calibration/basis solution and said mixed unknown/basis solution, following each full cycle of applied electrical potential.

7. A method according to claim 6, further comprising the steps of:
   (m) adding in step (b) said predetermined amount of standard solution to a first defined volume of said basis solution; and
   (n) adding in step (f) said predetermined amount of working solution to a second volume of said basis solution, such that the amount of working solution added to said second volume is in direct proportion to the amount of standard solution added to said first volume.

* * * * *